US005968808A

United States Patent [19]
Jackson

[11] Patent Number: 5,968,808
[45] Date of Patent: Oct. 19, 1999

[54] **METHOD FOR PRODUCING DESICCATION TOLERANT *PAECILOMYCES FUMOSOROSEUS* SPORES**

[75] Inventor: Mark A. Jackson, Peoria, Ill.

[73] Assignee: The United States of America as represented by Secretary of Agriculture, Washington, D.C.

[21] Appl. No.: 08/944,245

[22] Filed: Oct. 6, 1997

Related U.S. Application Data

[63] Continuation of application No. 08/623,915, Mar. 28, 1996, abandoned, which is a continuation-in-part of application No. 08/499,481, Jul. 7, 1995, abandoned.

[51] Int. Cl.[6] .......... C12N 1/14
[52] U.S. Cl. .......... 435/254.1; 435/256.8; 424/93.5
[58] Field of Search .......... 435/254.1, 911, 435/256.8; 424/93.5

[56] References Cited

U.S. PATENT DOCUMENTS 5,360,607 11/1994 Eyal et al. .......... 424/93.5

OTHER PUBLICATIONS

Bidochka, M. J., T. A. Pfeifer, and G. G. Khachatourians. 1987. Development of the Entomopathogenic fungus *Beauveria bassiana* in liquid cultures. Mycopathologia 99:77–873.

Hallsworth, J. E. and N. Magan. 1994. Effects of KCI concentration on accumulation of acyclic sugar alcohols and trehalose in conidia of three entomopathogenic fungi. Letters Appl. Microbiol. 18:8–11.

Hegedus. D. D., M. J. Bidochka, G. S. Miranpuri, and G. G. Khachatourians. 1992. A comparison of the virulence, stability and cell–wall–surface characteristics of three spore types produced by the entomopathogenic fungus *Beauveria bassiana*. Appl. Microbiol. Biotechnol. 36:785–789.

Inch, J. M. M. and A. P. J. Trinci. 1987. Effects of water activity on growth and sporulation of *Paecilomyces farinosa* in liquid and solid medium. *J. Gen. Microbiol.* 133: 247–252.

Inch. J. M. M., A. M. Humphreys, A. P. J. Trinci, and A. T. Gillespie. 1986. Growth and blastospore formation by *Paecilomyces fumosoroseus,* a pathogen of brown planthopper (Nilaparvata lugens). Trans. Br. Mycol. Soc. 87:215–222.

Jackson, M. A. and D. A. Schisler. 1992. The composition and attributes of *Colletotrichum truncatum* spores are altered by the nutritional environment. Appl. Environ. Microbiol. 58:2260–2265.

Jackson, M. A. and R. J. Bothast. 1990. Carbon concentration and carbon to nitrogen ratio influence submerged culture conidiation by the potential bioherbicide *Colletotrichum truncatum* NRRL 13737. Appl. Environ. Microbiol. 56:3435–3438.

Jackson, M. A., P. J. Slininger, and R. J. Bothast. 1989. Effect of zinc, iron, cobalt, and manganese on *Fusarium moniliforme* NRRL 13616 growth and *fusarin C* biosynthesis in submerged cultures. Appl. Environ. Microbiol. 55:649–655.

Jaronski, S. T. 1986. Commerical development of deuteromycetous fungi of arthropods: a critical appraisal. In *Fundamental and Applied Aspects of Invertebrate Pathology* eds. Samson, R. A., J. M. Vlak, and R. Peters. Foundation of the Fourth International Colloquim of Invertebrate Pathology, Wageningen, Netherlands.

Jin, X., G. E. Harman, and A. G. Taylor. 1991. Conidial biomass and desciccation tolerance of *Trichoderma harzianum* produced at different medium water potentials. Biological control 1: 237–243.

Lane, B. S., A. P. J. Trinci, and A. T. Gillespie. 1991. Influence of cultural conditions on the virulence of conidia and blastospores of *Beauveria bassiana* to the green leafhopper, Nephotettix virescens. Mycol. Res. 95:829–833.

Latge, J–P, R. A. Hall, R. I. Cabrera, and J. C. Kerwin. 1986. Liquid fermentation of entomopathogenic fungi. In *Fundamental and Applied Aspects of Invertebrate Pathology* eds. Samson, R. A., J. M. Vlak, and D. Peters. Fourth International Colloquim of Invertebrate Pathology, Wageningen, Netherlands.

Puterka, G. J., R. A. Humber, and T. J. Poprawski. 1994. Virulence of fungal pathogens (imperfect fungi: hyphomycetes) to pear psylla (homoptera: psyllidae). Environ. Entomol. 23:514–520.

Schisler, D. A., M. A. Jackson, and R. J. Bothast. 1990. Influence of nutrition during conidiation of *Colletotrichum trucatum* on conidial germination and efficacy in inciting disease on *Sesbania exaltata* . Phytopathol. 81:587–590.

Smith, P. 1993. Control of *Bemisia tabaci* and the potential of *Paecilomyces fumosoroseus* as a biopesticide. Biocontrol News and Info. 14:7IN–78N.

Willis, D. 1987. Automated pre–column derivation of amino acids with o–phthalaldehyde by a reagent sandwiching technique. J. Chromatography 408:217–225.

Kirsop et al (ed) "Maintenace of Microorganisms", 1988, Academic Press, p. 87–90.

Atlas et al, "Handbook of Microbiological Media", 1994, CRC Press p. 106.

ATCC Catalogue of Fungi, 1991, p. 268.

*Primary Examiner*—Irene Marx
*Attorney, Agent, or Firm*—Arnold White & Durkee

[57] ABSTRACT

The present invention addresses the need to effectively produce high volumes of desiccation tolerant spores of fungal species such as *Paecilomyces fumosoroseus.* The present invention accomplishes this by providing a liquid culture media optimally enriched in nitrogen and carbon.

8 Claims, 4 Drawing Sheets

METHOD FOR PRODUCING DESICCATION TOLERANT *PAECILOMYCES FUMOSOROSEUS* SPORES

RELATED APPLICATION

This application is a continuation of application Ser. No. 08/623,915, filed on Mar. 28, 1996, now abandoned which is a continuation-in-part of U.S. patent application Ser. No. 08/499,481, filed Jul. 7, 1995, now abandoned.

FIELD OF THE INVENTION

The present invention pertains generally to methods and compositions related to the control of soft-bodied insect pests. The invention especially concerns methods and compositions for producing and drying desiccation-tolerant *Paecilomyces fumosoroseus* spores for controlling *Bemisia tabaci* (sweetpotato whitefly) and other soft-bodied insect pests.

BACKGROUND OF THE INVENTION

Myriad approaches have been pursued to control pests. Many of these approaches are directed to the control of pests that attack plants, most notably commercially valuable plants. Although much current agricultural research has pest control as its objective, pest destruction of plants and plant products is still a major problem.

Chemical pesticides in particular have been used extensively to control pests for many years. An awareness of recent problems associated with the use of chemical pesticides such as adverse effects on man and the environment has led to a focus on biological control alternatives to chemical pesticides. For instance, certain fungi have been identified to be pathogenic to different pests. Importantly, many fungi, unlike pathogenic bacteria, viruses and protozoa need not necessarily be ingested by the target insect to initiate disease, but instead usually invade through their host's cuticle.

Sweetpotato whitefly is a particularly serious insect pest worldwide. In Texas and California alone, agronomic losses exceed $250 million annually. The insect rapidly develops resistance to chemical pesticides and is not adequately controlled with current pest management practices.

Various strains of the fungus *Paecilomyces fumosoroseus* have been proposed as a possible biological control agent for sweetpotato whitefly. A significant constraint to the development of this fungus and other like fungi as biocontrol agents, however, is the availability of low-cost methods for producing infective propagules. Solid-substrate methods of producing spores from such fungi as *Paecilomyces fumosoroseus* have proven too costly for commercial consideration. Hence, liquid culture methods for producing spores are preferred.

Eyal et al. has described in U.S. Pat. No. 5,360,607 a submerged culture technique for growing the mycelium of *Paecilomyces fumosoroseus.* The grown mycelial biomass is harvested and then formed into dry prill which can be used directly on plants and soil or the prill can be used as a carrier for sporulation of conidia spores. However, to be an effective insecticidal agent, mycelia containing prill must be wetted, the fungus must grow and sporulate, and insects must contact the newly formed spores. It would be more advantageous to develop a method of producing a high volume of insecticidal spores (versus mycelium) which could be directly applied to insects and actively instigate insect kill without the need for sporulation and contact by the target insect.

Previous attempts to produce *Paecilomyces fumosoroseus* spores directly using liquid culture fermentation methods have yielded unstable spores which are desiccation intolerant and hence readily perish during drying. Clearly, there is a need to develop a method to rapidly produce high volumes of spores which are desiccation tolerant and have high survival rates after drying and storage. In particular, it would be useful to produce desiccation tolerant spores of *Paecilomyces fumosoroseus.*

SUMMARY OF THE INVENTION

The present invention addresses the need to effectively produce high volumes of desiccation tolerant spores of fungal species such as *Paecilomyces fumosoroseus.* Specifically, the invention provides a liquid culture medium which allows for the rapid production of a high volume of desiccation resistant fungal spores and a method of producing the same.

In a first general embodiment, the invention provides a liquid culture medium for producing a high concentration of desiccation resistant fungal spores, whereby the medium comprises a nitrogen source at a concentration between 8.1 grams/liter and less than 50 grams/liter. The nitrogen source is preferably selected from the group consisting of hydrolyzed casein, yeast extract, hydrolyzed soy protein, hydrolyzed cottonseed protein, hydrolyzed corn gluten protein, and other nitrogen sources.

In a preferred embodiment the nitrogen source is present at a concentration greater than 12.5 grams/liter and optimally, at a concentration between 13.2 grams/liter and 30 grams/liter. In an especially preferred embodiment, the liquid culture medium further comprises a carbon source greater than 20 grams/liter and most optimally, greater than or equal to 80 grams/liter. In a most preferred embodiment the liquid culture medium comprises a nitrogen source at a concentration between 13.2 grams/liter and 30 grams/liter and a carbon source greater than or equal to 80 grams/liter.

In a second general embodiment the invention provides a liquid culture medium for producing a high concentration of desiccation resistant *Paecilomyces fumosoroseus* spores whereby the medium comprises a nitrogen source present at a concentration between 8.1 grams/liter and less than 50 grams/liter.

The nitrogen source is preferably selected from the group consisting of hydrolyzed casein, yeast extract, hydrolyzed soy protein, hydrolyzed cottonseed protein, and hydrolyzed corn gluten protein.

In a preferred embodiment the nitrogen source is present at a concentration greater than 12.5 grams/liter and optimally, at a concentration between 13.2 grams/liter and 30 grams/liter. In an especially preferred embodiment, the liquid culture medium further comprises a carbon source greater than 20 grams/liter and most optimally, greater than or equal to 80 grams/liter. In a most preferred embodiment the liquid culture medium comprises a nitrogen source greater than 13.2 grams/liter and a carbon source greater than or equal to 80 grams/liter.

The present invention further contemplates a method of producing a high concentration of desiccation tolerant fungal spores, comprising the steps of inoculating liquid culture medium comprising a nitrogen source with fungal propagules, whereby the nitrogen source is between 8:1 and less than 50 grams/liter; incubating the propagules for a sufficient time to allow for maximum sporulation; collecting the resulting spores; and drying the spores.

The nitrogen source is preferably selected from the group consisting of hydrolyzed casein, yeast extract, hydrolyzed soy protein, hydrolyzed cottonseed protein, and hydrolyzed corn gluten protein.

In a preferred embodiment the nitrogen source is present at a concentration greater than 12.5 grams/liter and optimally, at a concentration between 13.2 grams/liter and 30 grams/liter. In an especially preferred embodiment, the liquid culture medium further comprises a carbon source greater than 20 grams/liter and most optimally, greater than or equal to 80 grams/liter. In a most preferred embodiment the liquid culture medium comprises a nitrogen source greater than 13.2 grams/liter and a carbon source greater than or equal to 80 grams/liter.

DETAILED DESCRIPTION OF THE INVENTION

Figure 1:
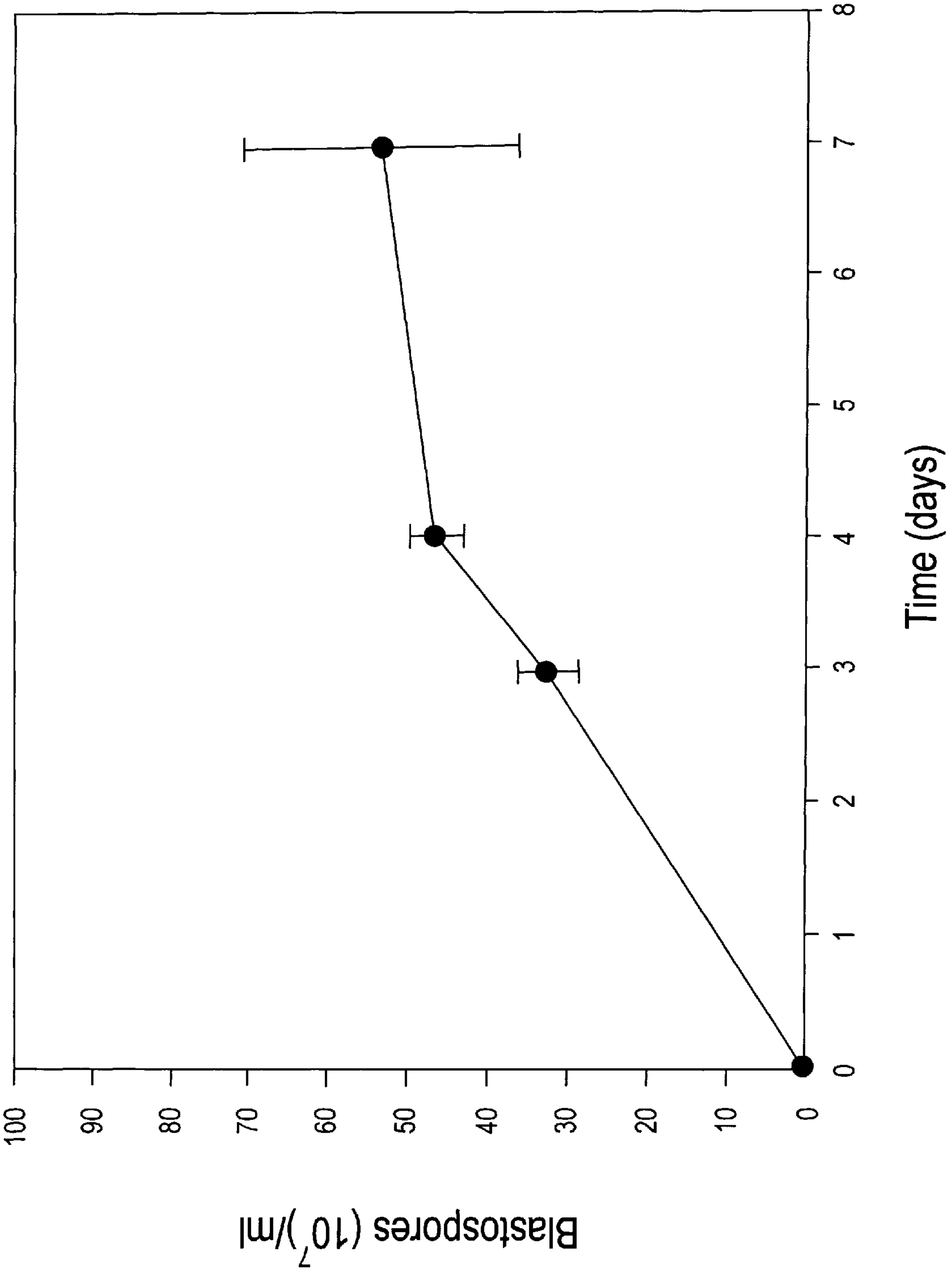
FIG. 1 depicts a time plot of blastospore production in medium containing 80 grams glucose/liter and 13.2 grams hydrolyzed casein/liter.

Fungi have recently been recognized as a valuable potential source for natural antiinsectons. Specifically, spores of certain fungi have been shown to contain metabolites that exert adverse physiological effects on insects. While spores from certain fungi hold great promise as biocontrol agents, a particular problem with such natural agents is the ability to rapidly produce a high volume of stable spores at low cost and which can be dried and stored without loss of activity.

A particularly serious insect pest is *Bemisia tabaci. Bemisia tabaci Gennadius* (Sweetpotato whitefly, cotton whitefly) has been reported to attack over 600 plants in warm climates worldwide (Smith, 1993). The ability of this phloem-feeding insect to reproduce rapidly can lead to heavy infestations which are capable of killing the host plant. Resistance to chemical insecticides and a lack of natural enemies has made the sweetpotato whitefly a serious pest in the Southern United States (Lacey, Kirk, and Hennessey, 1993). Predacious insects and entomopathogenic fungi are being evaluated as potential biological control agents for this pest. In general, the heavy use of insecticides in cropping systems where whiteflies are problematic has precluded the use of predacious insects. Fungi, which penetrate the cuticle of the insect, such as *Paecilomyces fumosoroseus,* appear to offer the best opportunity for biological control.

Many strains of *Paecilomyces fumosoroseus* and *Beauveria bassiana* have been isolated that are aggressive pathogens of numerous soft-bodied insects including *B. tabaci* (Lacey, Kirk, and Hennessey, 1993; Puterka, Humber, and Poprawski, 1994). Table 1 lists various *Paecilomyces fumosoroseus* strains and their countries of origin.

TABLE 1

Yield and Desiccation Tolerance of Liquid-Culture-Produced Spores of Various *Paecllomyces Fumosoroseus* Strains[1]

| *Paecilomyces Fumosoroseus* Strain ARSEF | OTHER DESIGNATION | *P. fumosoroseus* STRAIN LOCATION OF COLLECTION | YIELD (spores/ml) | FREEZE-DRYING[2] (% SURVIVAL) | VIABLE FREEZE-DRIED SPORES[2] (spores/ml) |
|---|---|---|---|---|---|
| 4490 | Ma8 | INDIA: PADAPPAI | 1.09E + 09 | 78 | 8.55E + 08 |
| 4491 | Ma17 | INDIA: PADAPPAI | 6.78E + 08 | 88 | 6.03E + 08 |
| 4492 | Ma18 | INDIA: PADAPPAI | 4.43E + 08 | 88 | 3.90E + 08 |
| 4493 | Ma19 | INDIA: PADAPPAI | 5.35E + 08 | 89 | 4.83E + 08 |
| 4494 | Ma20 | INDIA: PADAPPAI | 6.18E + 08 | 89 | 5.50E + 08 |
| 4495 | Ma21 | INDIA: PADAPPAI | 4.25E + 08 | 85 | 3.60E + 08 |
| 4496 | Ma22 | INDIA: PADAPPAI | 6.48E + 08 | 88 | 5.78E + 08 |
| 4497 | Ma27 | INDIA: PADAPPAI | 7.20E + 08 | 73 | 4.60E + 08 |
| | Pfr92111 | PAKISTAN: MULTAN | 8.65E + 08 | 76 | 6.38E + 08 |
| | Pfr92116 | PAKISTAN: MULTAN | 4.06E + 08 | 87 | 3.57E + 08 |
| 3377 | Pfr92117 | PAKISTAN: MULTAN | 7.00E + 08 | 86 | 6.00E + 08 |
| 3878 | Pfr92118 | PAKISTAN: MULTAN | 3.75E + 08 | 90 | 2.76E + 08 |
| | Pfr92119 | PAKISTAN: MULTAN | 5.95E + 08 | 78 | 4.43E + 08 |
| 3870 | Pfr92133 | NEPAL: KATMANDU VALLEY | 5.20E + 08 | 92 | 4.78E + 08 |
| | Pfr92134 | NEPAL: KATMANDU VALLEY | 4.48E + 08 | 82 | 3.75E + 08 |
| 3871 | Pfr92135 | NEPAL: KATMANDU VALLEY | 4.80E + 08 | 89 | 4.28E + 08 |
| | Pfr92136 | NEPAL: KATMANDU VALLEY | 4.76E + 08 | 92 | 4.36E + 08 |
| | Pfr92138 | NEPAL: KATMANDU VALLEY | 6.23E + 08 | 86 | 4.90E + 08 |
| 4480 | Pfr3660 | CALIFORNIA: EL CENTRO | 5.08E + 08 | 91 | 4.78E + 08 |
| 4481 | Pfr3663 | CALIFORNIA: | 3.40E + 08 | 95 | 3.28E + 08 |

TABLE 1-continued

Yield and Desiccation Tolerance of Liquid-Culture-Produced Spores of Various *Paecllomyces Fumosoroseus* Strains[1]

| *Paecilomyces Fumosoroseus* Strain ARSEF | OTHER DESIGNATION | LOCATION OF COLLECTION | YIELD (spores/ml) | FREEZE-DRYING[2] (% SURVIVAL) | VIABLE FREEZE-DRIED SPORES[2] (spores/ml) |
|---|---|---|---|---|---|
| | | *P. fumosoroseus* STRAIN | | | |
| 4489 | Pfr3698 | CALEXICO CALIFORNIA: CALEXICO | 4.65E + 08 | 96 | 4.48E + 08 |
| | Pfr3572 | TEXAS: McALLEN | 6.05E + 08 | 92 | 5.65E + 08 |
| | Pfr3594 | TEXAS: McALLEN | 3.93E + 08 | 82 | 3.40E + 08 |
| FPLSD[3] | (P > 0.05) = | | 3.53E + 08 | NSD[4] | NSD |

[1]SPORES COLLECTED FROM 4-DAY OLD CULTURES.
[2]SPORE VIABILITY DETERMINED BY 6 HOUR GERMINATION ASSAY IN POTATO DEXTROSE BROTH.
[3]FISHER'S PROTECTED LEAST SIGNIFICANT DIFFERENCE.
[4]NOT SIGNIFICANTLY DIFFERENT.

The feasibility of using *P. fumosoroseus* as biocontrol agents against sweetpotato whitefly is dependent on numerous biological constraints, including the ability to produce high concentrations of stable propagules at a reasonable cost (Jaronski, 1985; Latge et al., 1985). On solid substrates, *Paecilomyces fumosoroseus* and *Beauveria bassiana* strains produce abundant aerial conidia which are amenable to storage as dry preparations. In submerged culture, *Paecilomyces fumosoroseus, Paecilomyces farinosus,* and *Beauveria bassiana* are reported to produce high concentrations of spores (Bidochka, Pfeifer, and Khachatourians, 1987). Spores produced in liquid culture by various entomopathogenic fungi are typically larger than aerial conidia, are not amenable to simple drying techniques, and tend to perish more rapidly during storage (Inch et al., 1986; Inch and Trinci, 1987; Lane, Trinci, and Gillespie, 1991; Hegedus et al., 1992).

The present invention has focused on developing liquid culture techniques for producing desiccation tolerant spores such as spores from *Paecilomyces fumosoroseus* as well as of high concentrations of desiccation tolerant *Paecilomyces fumosoroseus* spores which were capable of infecting and killing the sweetpotato whitefly, *B. tabaci* and other soft bodied insects including Russian wheat aphid *Agropyron elongatum* and greenhouse whitefly (*Trialeurodes vaporariorum*).

Optimal Composition of Liquid Culture Medium for Spore Production

The impact of nutrition on submerged culture production of desiccation tolerant *Paecilomyces fumosoroseus* spores was evaluated by growing the fungus in media with differing carbon concentrations and carbon-to-nitrogen (CN) ratios. Spores were produced by inoculating liquid culture medium with fungal propagules; incubating the propagules, and collecting and drying the spores. Propagules are any living cells from a fungus that will propagate such as spores, mycelium or other fungal biomass.

TABLE 2

Evaluation of Liquid Culture Spore Production and Desiccation Tolerance by *Paecllomyces Fumosoroseus* ARSEF 4491 Using Various Media[1]

| GLUCOSE (g/L) | CASAMINO ACIDS (g/L) | AMINO ACID MIXIURE[4] (g/L) | [CARBON] (g/L) | CARBON -TO- NITROGEN RATIO | PRODUCTION[2] (106 spores/ml) | AIR-DRYING[3] (% SURVIVAL) |
|---|---|---|---|---|---|---|
| 80.0 | 13.2 | — | 39 | 36:1 | $580^{a\#}$ | $79^{a}$ |
| 3.6 | 1.7 | — | 4 | 30:1 | $46^{b,c}$ | $6^{b,c}$ |
| 7.8 | 5.0 | — | 4 | 10:1 | $94^{b,c}$ | $30^{b}$ |
| 9.2 | 0.6 | — | 4 | 80:1 | $15^{c}$ | $3^{c}$ |
| 15.6 | — | 3.2 | 8 | 15:1 | $130^{b}$ | $32^{b}$ |

[1]ALL MEDIA CONTAINED THE BASAL COMPONENTS LISTED IN THE MATERIALS AND METHODS.
[2]THREE-DAY-OLD CULTURES.
[3]AIR-DRYING OVERNIGHT WITH AIR (RH 20–30%). WHOLE CULTURE MIXED WITH 5% (w/v) DIATOMACEOUS EARTH.
[4]SYNTHETIC AMINO ACID MIXTURE. MIX-C, JACKSON & SLININGER. 1993. J. IND. MICROBIOL. 12:417–422.
[#]VALUES IN COLUMNS FOLLOWED BY DIFFERENT LETTERS ARE SIGNIFICANTLY DIFFERENT USING FISHER'S PROTECTED LSD.

other species. Various liquid culture medium were evaluated for producing *Paecilomyces fumosoroseus* spores based on spore yield and stability as a dry preparation. A liquid culture medium was identified which supported the rapid production As shown in Table 2, significantly higher concentrations of *Paecilomyces fumosoroseus* spores were produced in media which contained a high concentration of carbon and nitrogen. Under the conditions of this study, optimal production occurred at a carbon level of 80 grams glucose/liter and a nitrogen level of 13.2 grams Casamino acids/liter. Casamino acids are amino acids derived by hydrolyzing the protein casein. Media having 80 grams glucose/liter and 13.2 grams Casamino acids/liter will hereinafter be referred to as MS media. Such media, also enhanced spore tolerance to desiccation.

In addition to glucose, most carbohydrates tested in medium containing 13.2 grams hydrolyzed casein/liter allowed for excellent spore germination and desiccation resistance after freeze drying. Table 3 shows a comparison of *Paecilomyces fumosoroseus* ARSEF 4491 spore yield and desiccation tolerance when propagules were grown on various carbon sources.

TABLE 3

Comparison of Paecllomyces Fumosoroseus ARSEF 4491 spore yield and Desiccation Tolerance When Grown on Other Carbon Sources[1]

| | SPORE YIELD (spores/ml) | AFTER FREEZE-DRYING spore germination (%) |
|---|---|---|
| GLUCOSE | 6.7E + 08 | 82.5 |
| FRUCTOSE | 3.7E + 08 | 92.0 |
| SUCROSE | 5.0E + 08 | 72.5 |
| GALACTOSE | 2.9E + 08 | 86.5 |
| GLYCEROL | 7.4E + 08 | 92.0 |
| CITRATE | 1.9E + 08 | 71.0 |
| ACETATE | 0.0E + 00 | 0.0 |

[1]The standard production medium and conditions were used. 80 g Glucose/L is replaced by 80 g/L of the various carbon sources.

Likewise, suitable nitrogen sources are not limited to hydrolyzed casein. Table 4 shows that numerous nitrogen sources support the liquid culture production of high concentrations of spores with improved desiccation tolerance after drying. Benefical sources of nitrogen include yeast extract, hydrolyzed casein, soy protein, cottonseed protein and corn gluten protein.

TABLE 4

Effect of Nitrogen Source on *P. fumosoroseus* Blastospore Yield and Desiccation Tolerance[#]

| Nitrogen Source | Blastospore Yield (spores/ml) | After Freeze-drying (% germination)* | Viable spores/ml (after drying) |
|---|---|---|---|
| Yeast Extract | 9.9E + 08 | 79 | 7.8E + 08 |
| Enhancetone | 1.2E + 09 | 43 | 5.3E + 08 |
| Casamino Acids | 6.0E + 08 | 82 | 4.8E + 08 |
| Papaic Digest of Soy | 1.1E + 09 | 38 | 4.6E + 08 |
| Cottonseed Hydrolysate | 7.7E + 08 | 50 | 4.1E + 08 |
| Corn Gluten Hydrolysate | 5.6E + 08 | 58 | 3.4E + 08 |
| Corn Steep Liquor | 4.0E + 08 | 44 | 2.3E + 08 |
| Digest of Milk & Meat Protein | 4.4E + 08 | 50 | 1.9E + 08 |
| Distiller's Dried Grains & Solubles | 4.5E + 08 | 56 | 1.9E + 08 |
| Digest of Rice Flour | 1.0E + 08 | 15 | 1.8E + 08 |
| LSD P = 0.05 | 2.5E + 08 | 31 | 2.9E + 08 |
| LSD P = .01 | 3.4E + 08 | 42 | 3.9E + 08 |

[#]Basal salts liquid medium with 80 g glucose/L and 13.2 g nitrogen source/L. Incubated 28° C. and 300 rpm.
*6-hour germination assay - Potato Dextrose Broth, 28° C., 300 rpm.

The experiments that produced the data shown in Tables 3 and 4 were run using the standard production medium and conditions detailed in Examples 1 and 2 of this application.

When cultures were grown in media supplemented with glucose and Casamino acids in which the carbon concentration was held constant (4 g carbon/liter) and the CN ratio varied, lower concentrations of desiccation sensitive spores were produced. In medium with 4 g carbon/liter, spore concentrations were not significantly different regardless of the CN ratio of the medium and desiccation tolerance was only slightly better in spores produced in medium with a CN ratio of 10:1 when compared to spores produced in medium with a CN ratio of 80:1 (Table 2).

It is suspected that nitrogen depletion may limit sporulation since spore concentrations did not significantly increase after amino acids were utilized (FIG. 2). Furthermore, when glucose levels were held constant at 80 grams/liter, sporulation increased with increasing Casamino acid concentration up to 25 grams/liter as shown in Table 5. Upon further experimentation, premium sporulation was achieved with a Casamino acid concentration of 40 grams/liter and up to 50 grams/liter as shown in Table 5A. Specifically, 13.2 to 30 grams Casamino acids/liter appeared to be necessary for maximum spore yield while greater than or equal to 6.8 grams Casamino acids/liter and less than 50 grams/liter casamino acids appeared to be necessary for maximal viability after drying.

TABLE 5

Effect of Casamino Acid Concentration on Sporulation and Desiccation Tolerance of *Paecilomyces fumosoroseus* 4491 Blastospores[1]

| Casamino Acids (g/L) | Blastospore Yield[2] (spores/ml) | Viability After Drying[3] (% spore germination) | Viable Spores After Drying (spores/ml) |
|---|---|---|---|
| 25.0 | 4.0E + 07 | 59 | 2.4E + 07 |
| 20.0 | 7.5E + 08 | 85 | 6.3E + 08 |
| 15.0 | 4.3E + 08 | 76 | 3.3E + 08 |
| 13.2 | 4.6E + 08 | 83 | 3.7E + 08 |
| 11.4 | 2.7E + 08 | 79 | 2.2E + 08 |
| 9.6 | 2.4E + 08 | 85 | 2.0E + 08 |
| 6.8 | 1.5E + 08 | 78 | 1.2E + 08 |
| 5.0 | 8.5E + 07 | 58 | 4.8E + 07 |
| 3.2 | 6.7E + 07 | 49 | 3.0E + 07 |
| 1.4 | 5.3E + 07 | 10 | 4.8E + 06 |

[1]Cultures grown in basal salts liquid medium with vitamins and 80 g glucose/L.
[2]4 day-old cultures.
[3]Spores mixed with diatomaceous earth, dewatered, and air-dried at 25° C. and a relative humidity of 65%. Viability determined with 6-hour germination assay.

TABLE 5A

Effect of Casamino Acid Concentration on Sporulation and Desiccation Tolerance of *Paecilomyces fumosoroseus* 4491 Blastospores[1]

| Casamino Acids (g/L) | Blastospore Yield[2] (spores/mL) | Viability After Drying[3] (% spore germination) | Viable Spores After Drying (spores/mL) |
|---|---|---|---|
| 50 | 3.0E + 07 | ND[4] | ND |
| 40 | 6.4E + 08 | 56 | 3.9E + 08 |
| 30 | 7.3E + 08 | 71 | 5.2E + 08 |
| 25.0 | 8.9E + 08 | 68 | 6.1E + 08 |
| 20.0 | 7.2E + 08 | 80 | 5.8E + 08 |
| 15.0 | 5.8E + 08 | 68 | 3.9E + 08 |
| 13.2 | 5.8E + 08 | 79 | 4.6E + 08 |
| 10 | 4.4E + 08 | 31 | 1.3E + 08 |
| 5.0 | 3.4E + 08 | 6 | 2.0E + 07 |
| FPLSD[5] | 2.4E + 08 | 14 | 2.2E + 08 |

[1]Cultures grown in basal salts liquid medium with vitamins and 80 g glucose/L.
[2]Blastospores collected from 4-day old cultures.
[3]Viablity determined by 6-hour germination assay in potato dextrose broth for air-dried blastospores.

TABLE 5A-continued

Effect of Casamino Acid Concentration on Sporulation and Desiccation Tolerance of *Paecilomyces fumosoroseus* 4491 Blastospores[1]

| Casamino Acids (g/L) | Blastospore Yield[2] (spores/mL) | Viability After Drying[3] (% spore germination) | Viable Spores After Drying (spores/mL) |
|---|---|---|---|

[4]Not done. Too few spores were produced to conduct air-drying.
[5]Fisher's protected last significant difference. ($P \geq 0.05$)

Figure 2A:
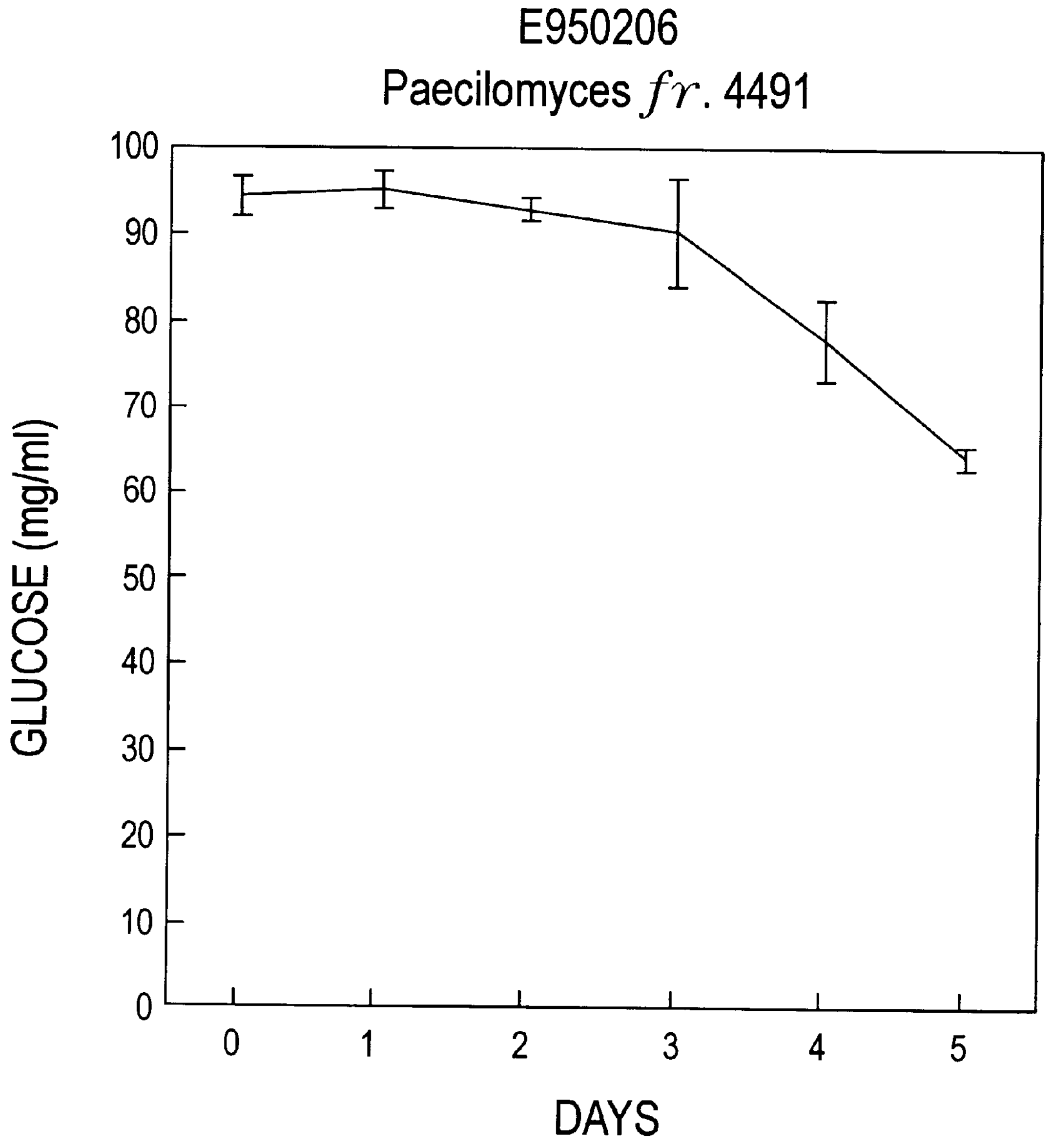
FIG. 2A depicts glucose utilization plotted against time for *Paecilomyces fumosoroseus* in medium containing 80 grams glucose/liter and 13.2 grams hydrolyzed casein/liter.
Figure 2B:
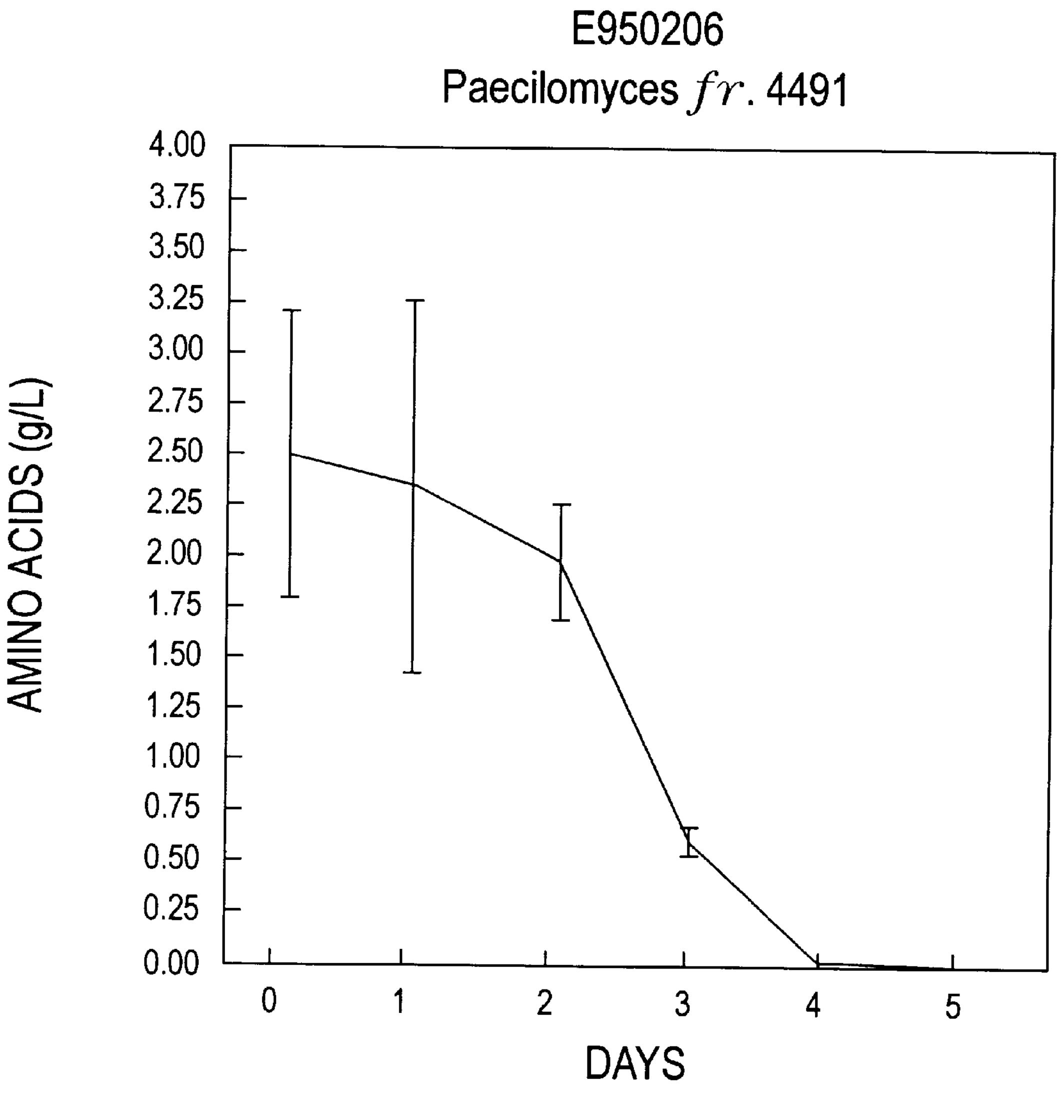
FIG. 2B depicts amino acid utilization plotted against time for *Paecilomyces fumosoroseus* in medium containing 80 grams glucose/liter and 13.2 grams hydrolyzed casein liter.

As shown in FIG. 1 and FIG. 2A and B, sporulation by cultures of *Paecilomyces fumosoroseus* 4491 in MS medium occurred rapidly and prior to glucose or amino acid exhaustion although Casamino acids were being rapidly utilized during days three and four when maximum sporulation was occurring. *Paecilomyces fumosoroseus* 4491 spore yields reached a maximum concentration, 3.4 to $6.8\times10^8$ spores/mL, after 4 days growth. FIG. 2A and 2B together depict the substrate utilization pattern of *Paecilomyces fumosoroseus* in MS medium. Specifically, FIG. 2A shows that MS medium contains excess carbohydrate and FIG. 2B shows that while Casamino acids were essentially depleted after 4 days growth, more than 70 g glucose/L remained (FIG. 2A). Amino acids, therefore, appear to be preferentially used by *Paecilomyces fumosoroseus* 4491 as a carbon and nitrogen source.

These results suggest that past reports on the instability of *Paecilomyces fumosoroseus* spores were due to spore formation under suboptimal nutritional conditions. By providing liquid grown *Paecilomyces fumosoroseus* cultures with the nutritional environment outlined herein, high concentrations of desiccation tolerant spores can be rapidly produced.

Comparison of the Ability of Various Strains of *Paecilomyces fumosoroseus* to Produce Desiccation Resistant Spores The ability of MS medium to support rapid and high volume sporulation of desiccation resistant spores is clearly not strain specific.

A comparison of 24 *Paecilomyces fumosoroseus* strains showed that MS medium supported the rapid production of high concentrations of desiccation tolerant spores (Table 1). Analysis of variance indicated that spore yield in all but three of the strains tested was not significantly different and that the total number and percentage of spores surviving freeze-drying were not significantly different for any of the strains tested.

Plate-counts were used to measure the viability of spores freeze-dried for storage while 6 hour germination assays in potato dextrose broth were used to assess the viability of air-dried spores and freeze-dried spores produced while screening the 24 different *Paecilomyces fumosoroseus* strains. A comparison of the 6 hour germination assay and plate count methods showed no significant differences in viability when comparing recently dried spore preparations (data not shown). Difficulties in plating air-dried spore-diatomaceous earth preparations made the 6-hour germination assay the method of choice for these preparations.

Figure 3:
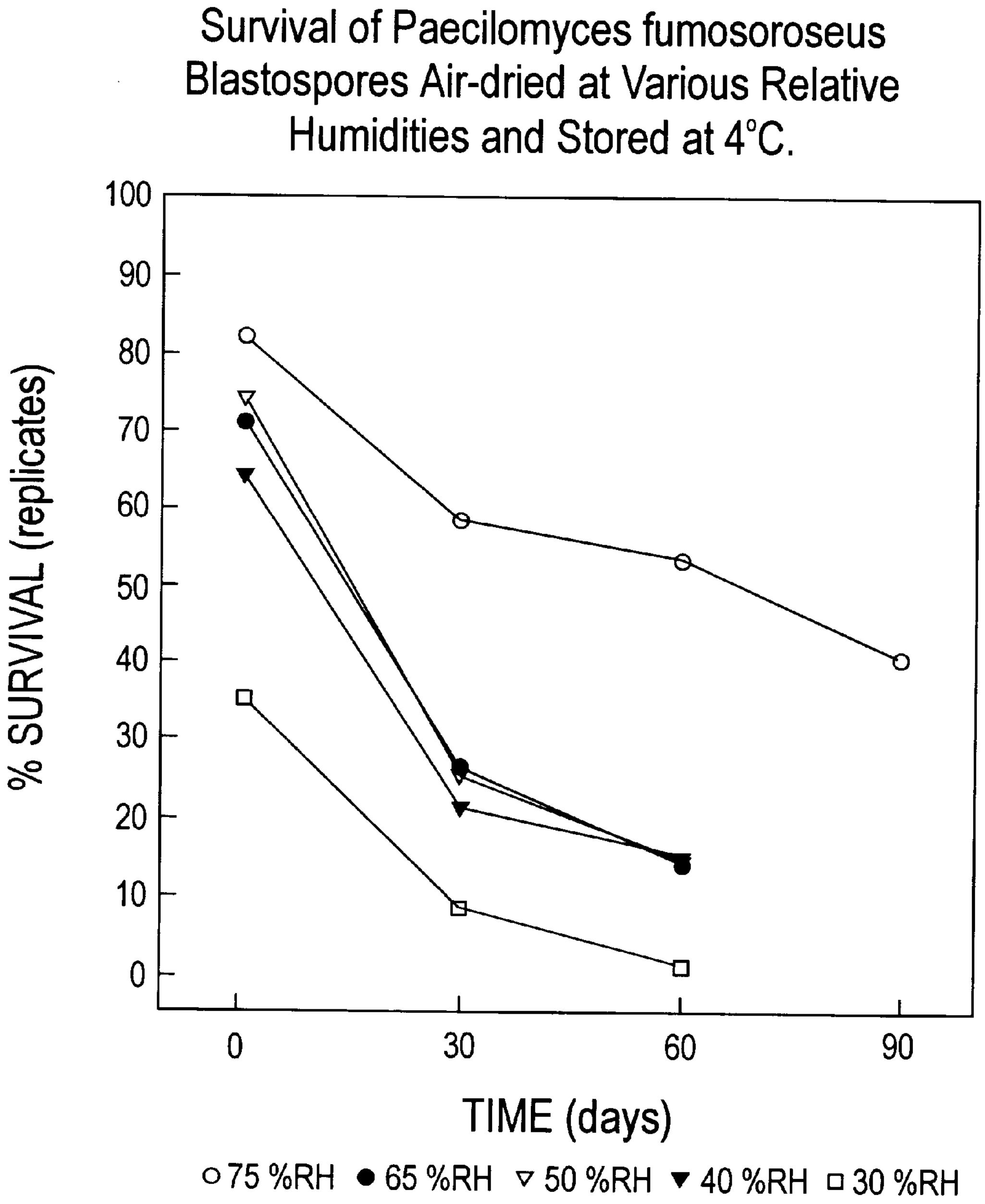
FIG. 3 depicts the percentage viability of spores air-dried at various relative humidities and stored at 4° C.

Air-dried preparations were stored in sealed plastic bags and freeze-dried spore preparations were stored in vacuum sealed ampules at either 4° C. or 22° C. After 5 months storage at 4° C., over 68% of the freeze-dried, vacuum sealed spores remained viable. Liquid culture produced spores air-dried at a relative humidity of 75% maintained 40% viability after 3 months storage at 4° C (FIG. 3).

The following examples are presented to describe preferred embodiments and utilities of the present invention and are not meant to limit the present invention unless otherwise stated in the claims appended hereto. For instance, although a majority of experiments involving the production of a high volume of desiccation resistant spores were performed utilizing *Paecilomyces fumosoroseus,* the medium and methods of the present invention will likely enhance sporulation and desiccation resistance for a variety of similar fungal species. Work with other fungi that are potential biological control agents, such as *Colletotrichum gloeosporioides* and *Fusarium moniliforme* have demonstrated that this medium can support rapid liquid culture sporulation. Other entomopathogenic fungi like *Paecilomyces fumosoroseus* which produce similar liquid culture spores will likely respond to this medium.

EXAMPLE 1: Strains and Culture Conditions

*Paecilomyces fumosoroseus* strains were obtained from various locations. Table 1 lists the various strains and their origin. Stock cultures were grown as single spore isolates on potato dextrose agar (PDA), cut into 1 $mm^2$ agar plugs and stored in 10% glycerol at −80° C. *Conidial inocula* were produced by inoculating PDA plates with conidial suspension from frozen stock cultures. Submerged cultures were inoculated with conidia from rinsed PDA plates to achieve a final concentration of $5\times10^4$ conidia/mL. Spore concentrations were determined microscopically with a hemocytometer. Liquid cultures were grown at 28° C. and 300 rpm in a rotary shaker incubator (100 mL in 250 mL baffled flasks). Replicate flasks were used for all treatments and all experiments were repeated at least twice.

EXAMPLE 2: Media Compositions

Media with various carbon sources, carbon concentrations, carbon-to-nitrogen (CN) ratios, and nitrogen sources were tested for their impact on *Paecilomyces fumosoroseus* spore yield and stability. The basal component of all medium tested contained per liter: $KH_2PO_4$, 2.0 g; $CaCl_2$—$2H_2O$, 0.4 g; $MgSO_4$—$7H_2O$, 0.3 g; $CoCl_2$—$6H_2O$, 37 mg; $FeSO_4$—$7H_2O$, 50 mg; $MnSO_4$—$H_2O$, 16 mg; $ZnSO_4$—$7H_2O$, 14 mg; thiamin, riboflavin, pantothenate, niacin, pyridoxamine, thiotic acid, 500 $\mu$g each; folic acid, biotin, vitamin $B_{12}$, 50 $\mu$g each. All medium had an initial pH of 5.5 and pH was uncontrolled during culture growth. The various carbon sources tested were autoclaved separately. The medium tested contained various carbon and nitrogen sources at differing concentrations as noted in the respective tables, graphs, and text.

EXAMPLE 3: Substrate Utilization

High performance liquid chromatography was used to measure glucose concentrations in culture supernatants, as previously described (Jackson, Slininger & Bothast, 1989). The concentration of 15 amino acids was measured in culture supernatants as o-phthalaldehyde derivatives using reverse-phase HPLC. These amino acids were aspartic acid, glutamic acid, serine, histidine, glycine, threonine, arginine, alanine, tyrosine, methionine, valine, phenylalanine, isoleucine, leucine, and lysine. The sum of the concentrations of the 15 amino acids was used as an approximation for the amino acid concentration in the culture supernatant.

EXAMPLE 4: Drying and Storage Studies

Liquid culture produced *Paecilomyces fumosoroseus* spores were dried using two methods: air-drying and freeze-drying. A high percentage of *Paecilomyces fumosoroseus* spores produced in MS medium survived air-drying (79±12.4%) and freeze-drying (86±10.6%). Statistical analyses of these results showed no significant differences in initial survival after air-drying or freeze-drying for *Paecilomyces fumosoroseus* 4491 spores produced in MS medium. In air-drying experiments, whole cultures were harvested after 3 days growth and mixed with 5% (w/v) diatomaceous earth (HYFLO, Celite Corp.). In subsequent air drying and freeze drying experiments where stability during storage and biocontrol efficacy were being evaluated, spores were separated from the mycelia by passing the culture through a double layer of cheesecloth twice. Air-drying experiments involved mixing the conidial suspension with 5% diatomaceous earth, filtering off the excess liquid, and drying the filter cake in a biological containment hood (20–30% RH) overnight to 1–5% moisture. Studies which evaluated the impact of the relative humidity (RH) of the drying air on spore survival were performed in a humidity controlled plant growth chamber at 25° C. For storage studies, air-dried spore preparations were kept in plastic bags at temperatures of 4° C. The viability of air-dried *Paecilomyces fumosoroseus* spores was assessed by adding dried spores to potato dextrose broth and measuring one hundred spores for germ tube formation after 6 hours incubation at 28° C. and 300 rpm in a rotary shaker incubator.

For freeze-drying experiments, spore suspensions were mixed (1:1) with a solution containing 20% lactose and 2% bovine serum albumin (BSA) to produce a spore mixture in 10% lactose, 1% BSA. Freeze-drying was performed in a tray dryer (Durastop-MP, FTS Systems) using an automatic-eutectic drying program. This program determined the eutectic point of the sample and set drying conditions based on this information, monitored the primary and secondary drying process, and determined when the drying process was completed. Ten milliliter vials containing 2 mL spore suspensions were used in all studies. At the end of the freeze-drying cycle, vials were sealed under vacuum and stored at 4° C. or 22° C. The viability of freeze-dried spores was assessed in two ways. For long-term storage studies, spore survival was measured by plate counts on potato dextrose agar incubated at 28° C. Prior to plating, freeze-dried spores were rehydrated for one hour at room temperature and diluted with sterile 0.004% phosephaste buffer. When screening various *Paecilomyces fumosoroseus* strains for spore production and stability after drying, the viability of freeze-dried spores was assessed by the 6 hour germination method previously described for air-dried spores.

EXAMPLE 5: Bioassays

Biocontrol efficacy studies against *B. tabaci* were performed with air-dried, liquid culture produced spores of *Paecilomyces fumosoroseus* ARSEF 4491. Various concentrations of air-dried spore:diatomaceous earth preparations were mixed with water and applied to whitefly-infested hibiscus leaves with a tower sprayer. Solid substrate produced aerial conidia of *Paecilomyces fumosoroseus* ARSEF 3699 and of *Beauveria bassiana* ARSEF 252 were used as controls in each experiment. An additional control of diatomaceous earth mixed with spent medium and dried in the same manner as the spore suspensions, was also used in all experiments. Conidial suspensions were sprayed onto hibiscus leaf discs infested with *B. tabaci* pupae and water agar plates. After spraying, the leaf discs were incubated in moist petri plates. The number of viable *Paecilomyces fumosoroseus* spores sprayed per $mm^3$ were measured on water agar plates after 24 hours incubation. Mortality in *B. tabaci* pupae and adults was assessed. The $LD_{50}$ (conidia/$mm^2$) and the potency ratio ($LD_{50}$ *B. bassiana*/$LD_{50}$ *Paecilomyces fumosoroseus*) was used to evaluate biocontrol efficacy of the air-dried liquid culture produced spores and the plate-derived aerial conidia. Under the conditions of this assay, air-dried, liquid culture product *Paecilomyces fumosoroseus* spores incited significant disease in *B. tabaci* nymphs (Table 6). These air-dried *Paecilomyces fumosoroseus* spores had potency ratios ($LD_{50}$ *Beauveria bassiana:* $LD_{50}$ *Paecilomyces fumosoroseus*) which were 8 times higher than solid-substrate produced aerial conidia of *Paecilomyces fumosoroseus* 4491 and were 4 times higher than the *B. bassiana* ARSEF 252 standard strain (Table 6).

TABLE 6

Efficacy of Air-dried Spores of *Paecilomyces fumosoroseus* for Controlling Sweetpotato Whitefly (*Bemisia tabaci*)

| | $LD_{50}$ (spores/$mm^2$) | Potency Ratio ($LD_{50}$ *Beauveria bassiana*) ($LD_{50}$ *Paecilomyces fumosoroseus*) |
|---|---|---|
| Control | 172.9 | 0.54 |
| Aerial conidia | | |
| Liquid culture | 56.6 | 4.11 |
| Spores | 115.6 | 3.77 |
| Test 1 | | |
| Test 2 | | |

The improvement in biocontrol efficacy of *Paecilomyces fumosoroseus* spores compared to *Paecilomyces fumosoroseus* conidia and *B. bassiana* conidia was dramatic. Hegedus et al., 1992, showed that spore preparations of *B. bassiana* were more infective than aerial conidia on the migratory grasshopper, *Melanoplus sanguinipes.* Conversely, another study suggested that the hydrophobic nature of *B. bassiana* conidia increased the adherence of these propagules to the cuticle of the green leafhopper, *Nephotettix virescens,* and significantly improved the biocontrol efficacy of conidia compared to *B. bassiana* spores (Lane, Trinci and Gillespie, 1991). It is possible that the hydrophobicity issue is less important when dealing with sessile *B. tabaci* nymphs rather than mobile insects. The rapid germination rate of liquid culture produced spores compared to aerial conidia may have enhanced the efficacy of these propagules in infecting and killing *B. tabaci* nymphs.

REFERENCES

1. Bidochka, M. J., T. A. Pfeifer, and G. G. Khachatourians. 1987. Development of the entomopathogenic fungus *Beauveria bassiana* in liquid cultures. Mycopathologia 99:77–83.
2. Eyal, J., J. F. Walter, L. Osborne, and Z. Landa. Nov. 1, 1994. Method for production and use of pathogenic fungal preparation for pest control. U.S. Pat. No. 5,360, 607.
3. Hallsworth, J. E. and N. Magan. 1994. Effects of KCI concentration on accumulation of acyclic sugar alcohols and trehalose in conidia of three entomopathogenic fungi. Letters Appl. Microbiol. 18:8–11.
4. Hegedus. D. D., M. J. Bidochka, G. S. Miranpuri, and G. G. Khachatourians. 1992. A comparison of the virulence, stability and cell-wall-surface characteristics of three spore types produced by the entomopathogenic fungus *Beauveria bassiana.* Appl. Microbiol. Biotechnol. 36:785–789.
5. Inch, J. M. M. and A. P. J. Trinci. 1987. Effects of water activity on growth and sporulation of *Paecilomyces*

*farinosa* in liquid and solid medium. J. Gen. Microbiol. 133:247–252.

6. Inch. J. M. M., A. M. Humphreys, A. P. J. Trinci, and A. T. Gillespie. 1986. Growth and blastospore formation by *Paecilomyces fumosoroseus,* a pathogen of brown planthopper (*Nilaparvata lugens*). Trans. Br. Mycol. Soc. 87:215–222.
7. Jackson, M. A. and D. A. Schisler. 1992. The composition and attributes of *Colletotrichum truncatum* spores are altered by the nutritional environment. Appl. Environ. Microbiol. 58:2260–2265.
8. Jackson, M. A. and R. J. Bothast. 1990. Carbon concentration and carbon to nitrogen ratio influence submerged culture conidiation by the potential bioherbicide *Colletotrichum truncatum* NRRL 13737. Appl. Environ. Microbiol. 56:3435–3438.
9. Jackson, M. A., P. J. Slininger, and R. J. Bothast. 1989. Effect of zinc, iron, cobalt, and manganese on *Fusarium moniliforme* NRRL 13616 growth and fusarin C biosynthesis in submerged cultures. Appl. Environ. Microbiol. 55:649–655.
10. Jaronski, S. T. 1986. Commercial development of deuteromycetous fungi of arthropods: a critical appraisal. In "Fundamental and Applied Aspects of Invertebrate Pathology" eds. Samson, R. A., J. M. Vlak, and R. Peters. Foundation of the Fourth International Colloquim of Invertebrate Pathology, Wageningen, Netherlands.
11. Jin, X., G. E. Harman, and A. G. Taylor. 1991. Conidial biomass and desiccation tolerance of *Trichoderma harzianum* produced at different medium water potentials. Biological Control 1:237–243.
12. Lacey, L. A., A. A. Kirk, and R. D. Hennessey. 1993. Foreign exploration for natural enemies of *Bemisia tabaci* and implementation in integrated control programs in the United States. Proc. 3rd International Conference on Pests in Agriculture. Montpellier, France, pp. 351–360.
13. Lane, B. S., A. P. J. Trinci, and A. T. Gillespie. 1991. Influence of cultural conditions on the virulence of conidia and blastospores of *Beauveria bassiana* to the green leafhopper, *Nephotettix virescens.* Mycol. Res. 95:829–833.
14. Latge, J-P, R. A. Hall, R. I. Cabrera, and J. C. Kerwin. 1986. Liquid fermentation of entomopathogenic fungi. In "Fundamental and Applied Aspects of Invertebrate Pathology" eds. Samson, R. A., J. M. Vlak, and D. Peters. Fourth International Colloquim of Invertebrate Pathology, Wageningen, Netherlands.
15. Puterka, G. J., R. A. Humber, and T. J. Poprawski. 1994. Virulence of fungal pathogens (imperfect fungi: hyphomycetes) to pear psylla (homoptera: psyllidae). Environ. Entomol. 23:514–520.
16. Schisler, D. A., M. A. Jackson, and R. J. Bothast. 1990. Influence of nutrition during conidiation of *Colletotrichum truncatum* on conidial germination and efficacy in inciting disease on *Sesbania exaltata.* Phytopathol. 81:587–590.
17. Smith, P. 1993. Control of *Bemisia tabaci* and the potential of *Paecilomyces fumosoroseus* as a biopesticide. Biocontrol News and Info. 14:7IN–78N.
18. Willis, D. 1987. Automated pre-column derivation of amino acids with o-phthalaldehyde by a reagent sandwiching technique. J. Chromatography 408:217–225.

What is claimed is:

1. A method of producing from *Paecilomyces fumosoroseus* a high concentration of desiccation tolerant fungal spores, comprising the steps of:

a) inoculating a liquid culture medium comprising a carbon source and a nitrogen source with fungal propagules of *Paecilomyces fumosoroseus,* said nitrogen source having a concentration between 8.1 grams/liter and 50 grams/liter provided that said nitrogen source is not corn steep liquor digest of milk and meat protein, distiller's dried grains, or solubles and digest of rice flour and said carbon source having a concentration greater than 20 grams/liter;

b) incubating the propagules for a sufficient time to allow for maximum sporulation;

c) collecting the resulting spores; and d) drying the spores.

2. The method of claim 1, wherein the nitrogen source is selected from the group consisting of hydrolyzed casein, yeast extract, hydrolyzed soy protein, hydrolyzed cottonseed protein, and hydrolyzed corn gluten protein.

3. The method of claim 2, wherein the liquid culture medium comprises a nitrogen source present at a concentration greater than 12.5 grams/liter and less than 50 grams/liter.

4. The method of claim 2, wherein the liquid culture medium comprises a nitrogen source present at a concentration between 13.2 grams/liter and 30 grams/liter.

5. The method of claim 4, wherein the liquid culture medium further comprises a carbon source at a concentration greater than or equal to 80 grams/liter.

6. The method of claim 2, wherein the liquid culture medium further comprises a carbon source at a concentration greater than or equal to 80 grams/liter.

7. The method of claim 1 wherein said spores are air dried at a relative humidity of 75%.

8. The method of claim 1 wherein said spores are freeze dried in a spore suspension of 10% lactose and 1% soluble protein.

* * * * *

UNITED STATES PATENT AND TRADEMARK OFFICE

CERTIFICATE OF CORRECTION

PATENT NO. : 5,968,808

DATED : October 19, 1999

INVENTOR(S) : Jackson

It is certified that error appears in the above-identified patent and that said Letters Patent is hereby corrected as shown below:

Title page, item [54] and col. 1, delete "*FUMOSOROSEUS*SPORES" and insert --*FUMOSOROSEUS* SPORES--

Signed and Sealed this

Seventh Day of March, 2000

Attest:

Q. TODD DICKINSON

Attesting Officer

*Commissioner of Patents and Trademarks*

UNITED STATES PATENT AND TRADEMARK OFFICE

CERTIFICATE OF CORRECTION

PATENT NO.: 5,968,808

DATED: October 19, 1999

INVENTOR(S): Jackson

It is certified that errors appear in the above-identified patent, and that said Letters Patent is hereby corrected as shown below.

Column 14, Claim 1, line 23, after "liquor" insert --,--

Column 14, Claim 1, line 25, after "flour" insert --,--

Signed and Sealed this

Second Day of May, 2000

Attest:

Q. TODD DICKINSON

*Attesting Officer* *Director of Patents and Trademarks*